United States Patent [19]

Popper et al.

[11] 4,181,672
[45] Jan. 1, 1980

[54] PROCESS FOR PREPARING METAL CHELATES

[75] Inventors: Felix B. Popper; Jeremiah B. McCarthy, both of Nashua; James R. Hart, Merrimack, all of N.H.

[73] Assignee: W. R. Grace & Co., New York, N.Y.

[21] Appl. No.: 837,249

[22] Filed: Sep. 27, 1977

[51] Int. Cl.$^2$ .......................... C07F 13/00; C07F 3/06
[52] U.S. Cl. ............................ 260/429 J; 260/429 R; 260/429.9; 562/571; 562/572
[58] Field of Search ............ 260/429 J, 429.9, 429 R; 562/571, 572

[56] References Cited

U.S. PATENT DOCUMENTS

| | | | |
|---|---|---|---|
| 3,337,607 | 8/1967 | Wollensak | 562/572 |
| 3,644,444 | 2/1972 | Popper et al. | 260/429 J |
| 3,681,416 | 8/1972 | Miller et al. | 260/429 J |
| 3,687,992 | 8/1972 | Feiler et al. | 260/429 J |
| 3,715,393 | 2/1973 | Ribaldone et al. | 562/572 |
| 3,758,534 | 9/1973 | Popper et al. | 260/429 J |
| 3,966,803 | 6/1976 | Vogt et al. | 562/572 |
| 4,116,991 | 9/1978 | Leneuf | 260/429 J |

Primary Examiner—Helen M. S. Sneed
Attorney, Agent, or Firm—Elton Fischer; Donald G. Marion

[57] ABSTRACT

An aqueous solution of a chelate of: (a) at least one metal selected from a first group consisting of: (i) magnesium; (ii) calcium; (iii) zinc; and (iv) manganese (II); and (b) at least one chelating agent selected from a second group consisting of moieties of: (i) ethylenediaminetetraacetic acid; (ii) nitrilotriacetic acid; (iii) diethylenetriaminepentaacetic acid; and (iv) hydroxyethylethylenediaminetriacetic acid is prepared by a process comprising forming a first admixture by admixing in an aqueous system an oxide or hydroxide of at least one member of the first group and at least one member selected from a third group consisting of a tetraalkali metal salt of ethylenediaminetetraacetic acid, a trialkali metal salt of nitrilotriacetic acid, a pentaalkali metal salt of diethylenetriaminepentaacetic acid, and a trialkali metal salt of hydroxyethylethylenediaminetriacetic acid; forming a second admixture by admixing the first admixture and a nitrile selected from a fourth group consisting of ethylenediaminetetraacetonitrile, nitrilotriacetonitrile, and diethylenetriaminepentaacetonitrile, and heating the second admixture to form the chelate and evaporate by-product ammonia therefrom, the pH of the resulting substantially ammonia-free product can then be adjusted to about 5–9.5 or preferably 6–9 if it is not already within this pH range.

17 Claims, No Drawings

PROCESS FOR PREPARING METAL CHELATES

BACKGROUND OF THE INVENTION

This invention is in the field of metal chelates. More particularly, it is in the field of chelates of magnesium, calcium, zinc, and manganese with moieties of nitrilotriacetic acid (NTA), ethylenediaminetetraacetic acid (EDTA), diethylenetriaminepentaacetic acid (DTPA), and hydroxyethylethylenediaminetriacetic acid (HEDTA). Still more particularly, this invention is directed to a novel method for preparing such chelates.

Chelates prepared by the process of this invention are useful in treating soil to supply water soluble metals (e.g., magnesium, calcium, zinc, manganese) in chelated form to soil for agricultural purposes. These chelates are also useful to supply trace elements to animal feeds, and to supply water soluble metal ions (e.g., zinc ions) in chelated form to plating baths.

U.S. Pat. No. 3,681,416, Miller et al, teaches a process for preparing a metal chelate by reacting an aminonitrile with an alkali metal hydroxide and a metal oxide (e.g., zinc oxide) or hydroxide (e.g., calcium hydroxide) in an aqueous system.

U.S. Pat. No. 3,644,444, Popper et al, teaches a process for forming an aqueous solution of an alkali metal salt of a polyvalent metal chelate of a chelating aminoacetic acid from an admixture of water, an amine precursor of the chelating aminoacetic acid, formaldehyde, an alkali metal hydroxide, a cyanide of the polyvalent metal, and an alkali metal cyanide. Said patent also teaches a process for forming an aqueous solution of an alkali metal salt of a polyvalent metal chelate of a chelating aminoacetic acid from an admixture of water, an amine precursor of the chelating aminoacetic acid, formaldehyde, a polyvalent metal base selected from the group consisting of a hydroxide or an oxide of said polyvalent metal, an alkali metal hydroxide, and hydrogen cyanide, the amine precursor of the chelating aminoacetic acid. Similar teachings occur in U.S. Pat. No. 3,758,534, Popper et al.

SUMMARY

In summary, this invention is directed to a process for preparing an aqueous solution of a chelate of: (a) at least one metal selected from a first group consisting of: (i) magnesium; (ii) calcium; (iii) zinc; and (iv) manganese(II); and (b) at least one chelating agent selected from a second group consisting of moieties of: (i) ethylenediaminetetraacetic acid; (ii) nitrilotriacetic acid; (iii) diethylenetriaminepentaacetic acid; and (iv) hydroxyethylethylenediaminetriacetic acid, said process comprising:

(A) forming a first admixture by admixing in an aqueous system an oxide or hydroxide of at least one member of the first group and at least one member selected from a third group consisting of: (I) a tetraalkali metal salt of ethylenediaminetetraacetic acid; (II) a trialkali metal salt of nitrilotriacetic acid; (III) a pentaalkali metal salt of diethylenetriaminepentaacetic acid; and (IV) a trialkali metal salt of hydroxyethylethylenediaminetriacetic acid, the mole ratio of first group member to third group member being 2:0.5–1.5, preferably 2:1;

(B) admixing the first admixture and a member selected from a fourth group consisting of: (I) ethylenediaminetetraacetonitrile (EDTAN); (II) nitrilotriacetonitrile (NTAN); and (III) diethylenetriaminepentaacetonitrile (DTPAN) to form a second admixture, the mole ratio of first group member to fourth group member being 2:1.6–0.5, preferably 2:1.

(C) heating the second admixture to a temperature (e.g., 65° C. to the boiling point of the second admixture (said boiling point can be from about 100° C. or slightly higher to about 110° C. or slightly higher) effective for hydrolyzing the nitrile and evaporating by-product ammonia from the second admixture, and maintaining the second admixture at this temperature for a time (e.g., 1–4 hours, preferably 1–2.5 hours) effective for hydrolyzing the nitrile and evaporating the by-product ammonia from the system to form a substantially ammonia-free aqueous solution of the chelate; and (D) adjusting the pH of the resulting substantially ammonia-free aqueous solution of the chelate to about 5–9.5, preferably 6–9, if it is not already at 1 is pH and recovering the resulting product.

In an alternative and fully equivalent embodiment, the first admixture is heated to the temperature effective for hydrolyzing the nitrile (the fourth group member) before admixing the first admixture and the fourth group member. This temperature is the same temperature which is effective for evaporating (vaporizing) by-product ammonia from the system in Step "C" of the above Summary. Where using this fully equivalent method the heated first admixture and the fourth group member are admixed while maintaining the first admixture and the resulting second admixture at the temperature effective for: (i) hydrolyzing the nitrile; and (ii) evaporating by-product ammonia from the second admixture, and the second admixture is maintained at this temperature for a time effective for evaporating by-product ammonia therefrom. The pH is then adjusted, if required, as in Step "D" of said Summary.

DETAILED DESCRIPTION OF THE INVENTION

As indicated in the above Summary, it is generally preferred to provide the metal oxide (or hydroxide), the alkali metal salt of the chelating agent (AMS), i.e., the third group member of the above Summary, and the nitrile in amounts such that the mole ratio of metal oxide or hydroxide (or where using a mixture of a metal oxide and a metal hydroxide, of such oxide plus such hydroxide), to AMS to nitrile is 2:1:1 based on the amounts of metal oxide (or metal hydroxide or metal oxide plus metal hydroxide), AMS, and nitrile fed into the system. However, these ratios can be varied over fairly wide amounts.

For example, ratios of 2:0.5–1.5:1.6–0.5 are operable. It is generally preferred that the number of moles of AMS plus the number of moles of nitrile are substantially equal to the number of moles of metal oxide (or metal hydroxide or metal oxide plus metal hydroxide) charged into the reaction zone.

If said ratio is not substantially 2:1:1, an amount of AMS, or nitrile, or metal oxide (or metal hydroxide or metal oxide plus metal hydroxide) required to achieve such mole ratio can be added to the second admixture in Step "D" of the above Summary.

If the pH of the substantially ammonia-free second admixture prepared in Step "D" of the Summary is higher than desired, it can be lowered by adding an acid thereto. Such acid can be: (a) a mineral acid such as sulfuric acid, hydrochloric acid, phosphoric acid, or the like; (b) an organic acid such as acetic acid, propionic acid, methylbutyric acid, lactic acid, or the like; (c) an aminoacetic acid which can be the aminoacetic acid corresponding to the alkali metal salt of Step "A" of the above Summary, the aminoacetic acid corresponding to the aminoacetonitrile of Step "B" of the above Summary, or an aminoacetic acid which does not correspond to either said alkali metal salt or said aminoacetonitrile. Because of our disclosure other acids which are operable for lowering said pH will be readily apparent to those skilled in the art.

If the pH of the substantially ammonia-free second admixture prepared in Step "D" of the Summary is lower than desired, it can be increased by adding an alkali metal hydroxide thereto. The alkali metal hydroxide can be the alkali metal hydroxide corresponding to the cation of the alkali metal salt of Step "A" of the Summary or it can be another alkali metal hydroxide.

Sodium and potassium are preferred alkali metal ion components of the AMS; however, lithium ions are operable.

Although it is preferred to operate at temperatures no higher than the normal boiling point, somewhat higher temperatures are operable. Where using temperatures above the normal boiling point pressures above atmospheric are used. Such pressures can be attained with conventional pressure reactors (autoclaves and the like) having venting means which permit one to maintain pressures above atmospheric in the reactor while venting ammonia therefrom into an ammonia collecting means.

While the aminoacetic acids listed below are among those whose metal chelates are readily prepared by the process of our invention from the corresponding alkali metal salts and the corresponding aminoacetonitriles, it will be, because of our disclosure, readily apparent to those skilled in the art that chelates of other aminoacetic acids can be prepared by our method (process):

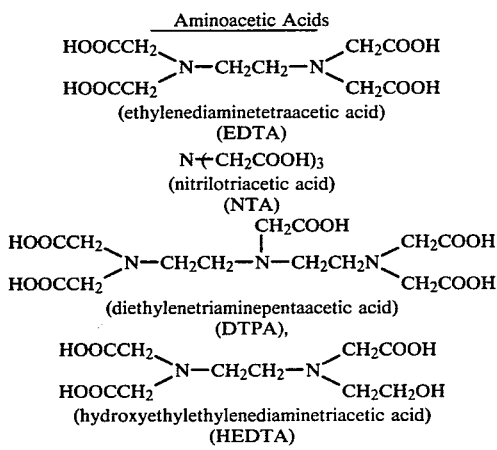

Aminoacetic Acids (ethylenediaminetetraacetic acid)
(EDTA)

N-(-CH$_2$COOH)$_3$
(nitrilotriacetic acid)
(NTA)

(diethylenetriaminepentaacetic acid)
(DTPA), (hydroxyethylethylenediaminetriacetic acid)
(HEDTA)

Because of our disclosure it will also be readily apparent to those skilled in the art that: (a) the alkali metal salt of the aminoacetic acid; and (b) the aminoacetonitrile do not have to correspond to the same aminoacetic acid. For example: (a) NTANa$_3$ or NTAK$_3$ can be used with diethylenetriaminepentaacetonitrile or with ethylenediaminetetraacetonitrile; and (b) the sodium or potassium salt of hydroxyethylethylenediaminetriacetic acid can be used with nitrilotriacetonitrile or ethylenediaminetetraacetonitrile. Still other combinations will, because of our disclosure, also be readily apparent to those skilled in the art; however, HEDTAN (hydroxyethylenediaminetriacetonitrile) should not be used.

It will also, because of our disclosure, be readily apparent to those skilled in the art that a mixture of two or more metal oxides or metal hydroxides can be used in our process. For example a mixture of zinc oxide, magnesium oxide, manganese(II) oxide, and calcium oxide can be used, and any or all of said oxides can be replaced in whole or in part with the corresponding hydroxide.

It will also be readily apparent to those skilled in the art that most other metal oxides and/or hydroxides which are capable of forming chelates with aminoacetic acids can be substituted in whole or in part for the oxides/hydroxides recited in the above Summary. However, it should be noted that aluminum oxide, aluminum hydroxide, iron(II) oxide, iron(II) hydroxide, iron(III) oxide, and iron(III) hydroxide cannot be substituted in whole or in part for the oxides and/or hydroxides recited in said Summary.

The following non-limiting examples, which were actually run, further illustrate the process of this invention.

EXAMPLE 1

833 g of an aqueous solution containing 1 mole of the trisodium salt of HEDTA (i.e., HEDTANa$_3$) was placed in a 2,500 ml beaker and diluted with an equal weight of water. A 2 mole (162.8 g) portion of zinc oxide was added to the diluted solution in the beaker while heating the resulting slurry to 95°-100° C. At 87° C. the pH of the slurry was 10.8.

0.9 mole (195 g) of ethylenediaminetetraacetonitrile (EDTAN) was added over a period of about an hour to the slurry in the beaker while maintaining the temperature of the resulting mixture at about 95°-100° C. The zinc oxide dissolved and the resulting mixture was boiled to evaporate by-product ammonia while adding water as necessary to maintain a substantially constant volume. When the solution was substantially free of ammonia, it was cooled to 60° C. and its pH was adjusted to 8 by adding 0.205 mole (59.5 g) of EDTA thereto. After adjusting the pH of said solution it (said solution) was diluted to 2,000 g with water, recovered, and analyzed at room temperature (ca. 23° C.). Results: (a) 6.63% total soluble (chelated and non-chelated) zinc; (b) 0.08% free soluble (non-chelated) zinc; (c) specific gravity 1.284; (d) pH 8.6; (e) no insoluble material; and (f) no free (uncombined) chelating agent.

EXAMPLE 2

The general method of Example 1 was repeated. However, in this instance a 1,000 g portion of a solution containing (in said 1,000 g portion) 1 mole of the tetrasodium salt of EDTA (EDTANa$_4$) was substituted for the 1 mole of HEDTANa$_3$ used in Example 1.

The reaction proceeded smoothly and 0.16 mole (47.2 g) of EDTA was required to bring the pH to 8 at 60° C.

Analysis of the product at room temperature (ca. 23° C.) gave the following results: (a) 6.2% total soluble zinc; (b) no free soluble zinc; (c) specific gravity 1.292; (d) pH 8.9; (e) no insoluble material; and (f) 1.97% free chelating agent reported as EDTA.

EXAMPLE 3

The general method of Example 2 was repeated; however, in this instance the EDTAN was replaced with 0.9 mole of nitrilotriacetonitrile (NTAN). 0.55 mole (147.5 g) of EDTA was required to adjust the pH at 60° C. Analysis of the product at room temperature after diluting to 2,000 g with water produced the following results: (a) 6.45% total soluble zinc; (b) 1.06% free soluble zinc; (c) pH 8.45; (d) no insoluble material; and (e) no free chelating agent.

EXAMPLE 4

The general method of Example 1 was repeated; however, in this instance a 1,250 g portion of a solution containing (in said 1,250 g portion) 1 mole of the pentasodium salt of DTPA (DTPANa$_5$) was substituted for the HEDTANa$_3$ used in Example 1. 0.29 mole (85.1 g) of EDTA was required to adjust the pH at 60° C. Analysis of the product at room temperature after diluting to 2,000 g with water produced the following results: (a) 6.35% total soluble zinc; (b) no free soluble zinc; (c) 2.88% free chelating agent reported as EDTA; and (d) no insoluble material.

EXAMPLE 5

The general method of Example 2 was repeated; however, in this instance the zinc oxide was replaced with 2.45 moles of manganese(II) oxide. 0.305 mole (89 g) of EDTA was required to adjust the pH at 60° C. Analysis of the product at room temperature after diluting to 2,000 g with water produced the following results: (a) 15.8 g of insoluble material; (b) 6.1% total soluble manganese; (c) 0.007% free soluble manganese; (d) no free chelating agent; and (e) pH 7.8.

EXAMPLE 6

The general method of Example 5 was repeated; however, in this instance 2 moles of manganese oxide was used. 0.208 mole (60.6 g) of EDTA was required to adjust the pH to 60° C. Analysis of the product at room temperature after diluting to 2,000 g with water produced the following results: (a) 2.1 g of insoluble material; (b) 5.44% total soluble manganese; (c) no free soluble manganese; (d) 1.38% free chelating agent reported as EDTA; and (e) pH 9.

EXAMPLE 7

The general method of Example 1 was repeated; however, in this instance the zinc oxide was replaced with 2 moles of manganese(II) oxide. 0.229 mole (66.8 g) of EDTA was required to adjust the pH at 60° C. Analysis of the product at room temperature after diluting to 2,000 g with water produced the following results: (a) no insoluble material; (b) 5.53% total soluble manganese; (c) no free soluble manganese; (d) 0.73% free chelate reported as EDTA; and (e) pH 8.4.

EXAMPLE 8

The general method of Example 4 was repeated; however, in this instance zinc oxide was replaced with 2 moles of calcium hydroxide using a grade of calcium hydroxide which on analysis was found to contain 96.5% Ca(OH)$_2$. 0.68 mole (78.4 g) of EDTA was required to adjust the pH at 60° C. The product was not analyzed because of the presence of a slime like precipitate which plugged the filter which was used in an attempt to remove said precipitate.

EXAMPLE 9

The general method of Example 2 was repeated; however, in this instance the zinc oxide was replaced with 2 moles of calcium hydroxide using a grade of calcium hydroxide which on analysis was found to contain 96.5% Ca(OH)$_2$. 0.215 mole (62.8 g) of EDTA was required to adjust the pH at 60° C. Analysis of the product at room temperature after diluting to 2,000 g with water produced the following results: (a) 5.0 g insoluble material; (b) 4.3% total soluble calcium; (c) no free soluble calcium; and (d) 1.46% free chelating agent reported as EDTA.

EXAMPLE 10

The general method of Example 1 was repeated; however, in this instance the HEDTANa$_3$ was replaced with 625 g of an aqueous solution containing 1 mole of the trisodium salt of nitrilotriacetic acid (NTANa$_3$) and the zinc oxide was replaced with 2 moles of magnesium oxide. 0.392 mole (141.7 g) of EDTA was required to adjust the pH at 60° C. Analysis of the product at room temperature after diluting to 2,000 g with water produced the following results: (a) 112.3 g insoluble material; (b) 1.88% total soluble magnesium; (c) 0.69% free soluble magnesium; and (d) no free chelating agent.

EXAMPLE 11

A 1 mole (416 g) portion of the pure tetrasodium salt of ethylenediaminetetraacetic acid dihydrate in the solid state was dissolved in a liter of water to form a first solution of said tetrasodium salt. Said first solution was free of excess alkali.

2 moles (162.8 g) of zinc oxide was added to the first solution and the resulting mixture was heated to about 90° C. and maintained at this temperature for about 3 hours while adding 0.9 moles (195 g) of ethylenediaminetetraacetonitrile (EDTAN) thereto. The resulting second solution was boiled until substantially free of ammonia. The substantially ammonia-free second solution was cooled to 60° C. at which temperature it had a pH of 10. EDTA, 0.117 mole (34.1 g), was added to adjust the pH of the substantially ammonia-free second solution to 7 and water was added to adjust the weight so that the resulting third solution contained 6.45% total soluble zinc (chelated zinc plus soluble free (non-chelated zinc)) reported as Zn. The third solution was recovered and analyzed for soluble free (non-chelated zinc); it was found to contain 0.03% free zinc reported as Zn.

The run reported in Example 11 was conducted to show that it is not free alkali metal hydroxide which saponified or the nitrile in Examples 1–10. As noted supra, the system used in Example 11 was free of excess caustic soda (i.e., it was free of caustic soda (NaOH) over that required by the stoichiometry for forming EDTANa$_4$) while each of the AMSs used in Examples 1–10 contained a small amount (ca. 1–2% based on the weight of the solution) of free caustic soda.

As used herein, the term mole has its generally accepted meaning, i.e.; a mole of a substance is the amount of said substance which contains the same number of molecules of the substance as there are $^{12}$C atoms in 12 g of pure $^{12}$C.

EDTAN means ethylenediaminetetraacetonitrile.
NTAN means nitrilotriacetonitrile.
DTPAN means diethylenetriaminepentaacetonitrile.

EDTANa₄ means the tetrasodium salt of ethylenediaminetetraacetic acid.

NTANa₃ means the trisodium salt of nitrilotriacetic acid.

HEDTANa₃ means the trisodium salt of hydroxyethylethylenediaminetriacetic acid.

DTPANa₅ means the pentasodium salt of diethylenetriaminepentaacetic acid.

AMS means alkali metal (e.g., Na, K, or Li) salt of a chelating agent. The above listed alkali metal salt are examples of AMSs.

EDTA means ethylenediaminetetraacetic acid.

NTA means nitrilotriacetic acid.

DTPA means diethylenetriaminepentaacetic acid.

HEDTA means hydroxyethylethylenediaminetriacetic acid.

We claim:

1. A process for preparing an aqueous solution of a chelate of: (a) at least one metal selected from a first group consisting of: (i) magnesium; (ii) calcium; (iii) zinc; and (iv) manganese(II); and (b) at least one chelating agent selected from a second group consisting of moieties of: (i) ethylenediaminetetraacetic acid; (ii) nitrilotriacetic acid; (iii) diethylenetriaminepentaacetic acid; and (iv) hydroxyethylethylenediaminetriacetic acid; said process comprising:

(A) forming a first admixture by admixing in an aqueous system an oxide or hydroxide of at least one member of the first group and at least one member selected from a third group consisting of: (I) a tetraalkali metal salt of ethylenediaminetetraacetic acid; (II) a trialkali metal salt of nitrilotriacetic acid; (III) a pentaalkali metal salt of diethylenetriaminepentaacetic acid; and (IV) a trialkali metal salt of hydroxyethylethylenediaminetriacetic acid;

(B) admixing the first admixture and a member selected from a fourth group consisting of: (i) ethylenediaminetetraacetonitrile; (II) nitrilotriacetonitrile; and (III) diethylenetriaminepentacetonitrile to form a second admixture;

(C) heating the second admixture to a temperature effective for hydrolyzing the nitrile and evaporating by-product ammonia from the second admixture, and maintaining the second admixture at this temperature for a time effective for hydrolyzing the nitrile and evaporating the by-product ammonia to form a substantially ammonia-free aqueous solution of the chelate; and (D) adjusting the pH of the resulting substantially ammonia-free aqueous solution of the chelate to about 5–9.5 and recovering the resulting product.

2. The process of claim 1 in which the chelate is a chelate of zinc.

3. The process of claim 1 in which the chelate is a chelate of manganese(II).

4. The process of claim 1 in which the chelate is a chelate of magnesium.

5. The process of claim 1 in which the chelate is a chelate of calcium.

6. The process of claim 1 in which the third group member is a tetraalkali metal salt of ethylenediaminetetraacetic acid.

7. The process of claim 1 in which the third group member is pentaalkali metal salt of diethylenetriaminepentaacetic acid.

8. The process of claim 1 in which the third group member is a trialkali metal salt of nitrilotriacetic acid.

9. The process of claim 1 in which the third group member is a trialkali metal salt of hydroxyethylethylenediaminetriacetic acid.

10. The process of claim 1 in which the second admixture is maintained at 65°–110° C. for 1–4 hours to vaporize by-product ammonia therefrom.

11. The process of claim 1 in which the second admixture boiled.

12. The process of claim 11 in which the second admixture is boiled for about 1–2.5 hours to evaporate ammonia therefrom.

13. The process of claim 1 in which the pH of the substantially ammonia-free aqueous solution of the chelate is adjusted to 6–9.

14. The process of claim 1 in which the fourth group member is ethylenediaminetetraacetonitrile.

15. The process of claim 1 in which the fourth group member is nitrilotriacetonitrile.

16. The process of claim 1 in which the fourth group member is diethylenetriaminepentaacetonitrile.

17. A process for preparing an aqueous solution of a chelate of: (a) at least one metal selected from a first group consisting of: (i) magnesium; (ii) calcium; (iii) zinc; and (iv) manganese(II); and (b) at least one chelating agent selected from a second group consisting of moieties of: (i) ethylenediaminetetraacetic acid; (ii) nitrilotriacetic acid; (iii) diethylenetriaminepentaacetic acid; and (iv) hydroxyethylenediaminetriacetic acid; said process comprising:

(A) forming a first admixture by admixing in an aqueous system an oxide or hydroxide of at least one member of the first group and at least one member selected from a third group consisting of: (I) a tetraalkali metal salt of ethylenediaminetetraacetic acid; (II) a trialkali metal salt of nitrilotriacetic acid; (III) a pentaalkali metal salt of diethylenetriaminepentaacetic acid; and (IV) a trialkali metal salt of hydroxyethylethylenediaminetriacetic acid;

(B) heating the first admixture to a temperature effective for: (1) hydrolyzing, in a later recited step, a nitrile selected from a fourth group consisting of: (I) ethylenediaminetetraacetonitrile; (II) nitrilotriacetonitrile; and (III) diethylenetriaminepentaacetonitrile; and (2) evaporating by-product ammonia therefrom in the later recited step;

(C) admixing the heated first admixture and the fourth group member while maintaining the first admixture and the resulting second admixture at the temperature effective for: (I) hydrolyzing the nitrile; and (II) evaporating by-product ammonia from the second admixture, and maintaining the second admixture at this temperature for a time effective for hydrolyzing the fourth group member and evaporating by-product ammonia therefrom to form a substantially ammonia-free solution of the chelate; and (D) adjusting the pH of the resulting substantially ammonia-free aqueous solution of the chelate to about 5–9.5 and recovering the resulting product.

* * * * *